United States Patent
Banerjee et al.

(10) Patent No.: US 9,778,202 B2
(45) Date of Patent: Oct. 3, 2017

(54) SYSTEMS AND METHODS FOR IMAGING CHARACTERISTICS OF A SAMPLE AND FOR IDENTIFYING REGIONS OF DAMAGE IN THE SAMPLE

(75) Inventors: Satyajit Banerjee, Kanpur (IN); Shyam Mohan, Kanpur (IN); Jaivardhan Sinha, Kanpur (IN)

(73) Assignee: Indian Institute of Technology Kanpur, Kanpur (IN)

( * ) Notice: Subject to any disclaimer, the term of this patent is extended or adjusted under 35 U.S.C. 154(b) by 963 days.

(21) Appl. No.: 13/878,944

(22) PCT Filed: Nov. 29, 2010

(86) PCT No.: PCT/IB2010/055472
§ 371 (c)(1),
(2), (4) Date: Mar. 12, 2014

(87) PCT Pub. No.: WO2012/049538
PCT Pub. Date: Apr. 19, 2012

(65) Prior Publication Data
US 2014/0176698 A1    Jun. 26, 2014

(30) Foreign Application Priority Data
Oct. 12, 2010   (IN) .......................... 2433/DEL/2010

(51) Int. Cl.
*G01N 21/88* (2006.01)
*G01N 27/90* (2006.01)
(Continued)

(52) U.S. Cl.
CPC ......... *G01N 21/8806* (2013.01); *G01N 21/21* (2013.01); *G01N 27/82* (2013.01);
(Continued)

(58) Field of Classification Search
CPC .... G01R 33/10; G01R 33/03; G01R 33/0322; G01R 33/032; G02B 21/0092;
(Continued)

(56) References Cited

U.S. PATENT DOCUMENTS 3,564,924 A    2/1971  De Sorbo et al.
4,625,167 A   11/1986  Fitzpatrick
(Continued)

FOREIGN PATENT DOCUMENTS

DE    4021359 A1 *  1/1992  .......... G01R 31/315
FR    2901025 A1   11/2007
(Continued)

OTHER PUBLICATIONS

Shamonin, M. et al., "Magneto-optical visualization of metal-loss defects in a ferromagnetic plate: experimental verification of theoretical modeling", Applied Optics, Jul. 2001, 3182-3189, vol. 40, 19.
(Continued)

*Primary Examiner* — Gordon J Stock, Jr.
(74) *Attorney, Agent, or Firm* — Moritt Hock & Hamroff LLP; Steven S. Rubin, Esq.

(57) ABSTRACT

Systems and methods for imaging characteristics of a sample and for identifying regions of damage in the sample are generally described. Some example systems and methods for non-destructive evaluation of regions of material may operate in a direct current (DC) mode in which the system directly images regions of material where weak structural damage has occurred by imaging a self magnetic field generated by a DC electric current coupled through the material. Some example systems may operate in an alternating current (AC) mode to image regions of material where damage has occurred by generating a time varying magnetic field due to AC excitation coils inducing eddy (Continued)

currents in the sample, and imaging a magnetic field generated by the eddy currents around the regions of damage. The systems may use magneto-optical imaging techniques (MOI) to measure and map the magnetic field and channels of current flow in the material, for example.

22 Claims, 11 Drawing Sheets

(51) Int. Cl.
*G01R 33/032* (2006.01)
*G01N 21/21* (2006.01)
*G01N 27/82* (2006.01)

(52) U.S. Cl.
CPC ............ *G01N 27/90* (2013.01); *G01R 33/032* (2013.01); *G01R 33/0322* (2013.01); *G01N 2021/218* (2013.01)

(58) Field of Classification Search
CPC ...... G01N 27/825; G01N 27/83; G01N 27/85; G01N 27/90; G01N 21/21; G01N 21/8806; G01N 27/82
See application file for complete search history.

(56) References Cited

U.S. PATENT DOCUMENTS

| | | | |
|---|---|---|---|
| 4,755,752 A | 7/1988 | Fitzpatrick | |
| 5,053,704 A * | 10/1991 | Fitzpatrick | G01R 33/0322 324/213 |
| 5,446,378 A | 8/1995 | Reich | |
| 5,574,368 A | 11/1996 | Horn | |
| 5,754,044 A * | 5/1998 | Tanielian | G01R 33/0325 324/213 |
| 5,773,973 A | 6/1998 | Horn | |
| 6,528,993 B1 * | 3/2003 | Shin | G02B 21/0016 324/223 |
| 6,972,562 B1 * | 12/2005 | Vlasko-Vlasov | B82Y 20/00 324/244.1 |
| 7,265,845 B2 | 9/2007 | Kochergin | |
| 8,159,216 B2 * | 4/2012 | Joubert | G01N 27/90 324/240 |
| 8,818,075 B2 * | 8/2014 | Placko | G01N 27/9046 382/149 |
| 2004/0218249 A1 | 11/2004 | Kochergin | |
| 2005/0171421 A1 * | 8/2005 | Eden | G01R 33/032 600/409 |
| 2006/0146328 A1 | 7/2006 | Decitre et al. | |
| 2006/0152216 A1 | 7/2006 | Higuchi | |
| 2010/0013468 A1 | 1/2010 | Joubert et al. | |
| 2010/0079908 A1 * | 4/2010 | Heidmann | G11B 5/455 360/110 |
| 2010/0170017 A1 * | 7/2010 | Heidmann | G01R 33/032 850/48 |
| 2011/0310387 A1 * | 12/2011 | An | G01N 21/21 356/369 |
| 2014/0225606 A1 * | 8/2014 | Endo | G01N 27/82 324/260 |

FOREIGN PATENT DOCUMENTS

| | | |
|---|---|---|
| JP | 60-76650 | 5/1985 |
| JP | 05-273322 | 10/1993 |
| JP | 2006215018 A | 8/2006 |
| JP | 2009-043964 | 2/2009 |
| JP | 2011163972 A | 8/2011 |
| KR | 1020080039781 | 7/2008 |

OTHER PUBLICATIONS

Bray, D.E. and R.K. Stanley, Nondestructive Evaluation: A Tool in Design, Manufacturing and Service; CRC Press, 1997, 527-546.
Cartz, L., Nondestructive Testing, Eddy Current Testing, ASM International, Materials Park, Ohio, 1995, p. 173-188.
NDT Encyclopedia, Nondestructive testing, retrieved from http://www.ndt.net/ndtaz/ndtaz.php on Jun. 25, 2010, 4 pages.
O' Brien, R. C. and W. B. James, A Review Of Nondestructive Testing Methods And Their Applicability To Powder Metallurgy Processing, MPIF Seminar on Prevention and Detection of Cracks in Ferrous P/M Pads, International Powder Metallurgy Conference and Exhibition, 1988, 17 pages, Hoeganaes Corporation.
Nondestructive Testing, Wikipedia, retrieved from http://en.wikipedia.org/wiki/Nondestructive_testing on Jun. 17, 2010, 7 pages.
Jooss, et al., Magneto-optical studies of current distributions in high-Tc superconductors; Rep. Prog. Phys., 2002, 651-788, 65.
Koblischka, M. R. and R. J. Wijngaarden, Magneto-optical investigations of superconductors, Supercond. Sci. Technol., 1995, 199-213, 8.
Polyanskii, A. A. et al., Visualisation of magnetic flux in magnetic material and high temperature superconductors using Faraday effect in ferrimagnetic garnet films, Nano-Crystalline and Thin Film Magnetic Oxides NATO Science Series vol. 72, 1999, pp. 353-370.
Griffith, David J., Introduction to electrodynamics—Chapter 5 Magnetostatics, 3rd edition, 1999, 202-254.
Banerjee, S. S. et al., Vortex Nanoliquid in High-Temperature Superconductors, Phys. Rev. Lett., 2004, 097002-1-4, 93.
U. Radtke et al., Application of magneto-optical method for real-time visualization of eddy currents with high spatial resolution for nondestructive testing, Optics and Lasers in Engineering, 2001, 251-268, 36.
Lacayo, G. and F. Ritter, Optical anisotropy and twin configuration in YBa2Cu3O7-x, Journal of Crystal Growth, 1993, pp. 199-204, vol. 126, Issues 2-3.
Kolb, P. W. et al, Optical imaging of multiphase coexistence in Nd1/2Sr1/2MnO3, Phys. Rev. B, 2004, 224415-1-5, 70.
Introduction to Nondestructive Testing, The American Society for Nondestructive Testing, retrieved from http://www.asnt.org/ndt/primer1.htm, 2010, 3 pages.
International Search Report for PCT application with application No. PCT/IB2010/055472, dated Mar. 3, 2011, 4 pages.

* cited by examiner

SYSTEMS AND METHODS FOR IMAGING CHARACTERISTICS OF A SAMPLE AND FOR IDENTIFYING REGIONS OF DAMAGE IN THE SAMPLE

CROSS-REFERENCE TO RELATED APPLICATIONS

The present application claims priority to Indian patent application serial number 2433/DEL/2010 filed on Oct. 12, 2010. The present application is a U.S. National Phase Application pursuant to 35 U.S.C. §371 of International Application No. PCT/IB2010/055472, filed on Nov. 29, 2010, the entire contents of which are incorporated by reference.

BACKGROUND

In numerous industrial applications, it is desirable to determine wear and tear of metallic parts. The metallic parts could be an inside bore of an artillery cannon, metallic parts of an aircraft engine or its body, metallic parts exposed to thermal cycling (periodic exposure to extreme heat and low temperatures, as in outer space) or a body of a car or any machine, for example.

Due to wear and tear, regions in material develop structural damage that may eventually develop into physical defects like cracks (either surface or sub-surface cracks or cracks deep inside the material). Such cracks can compromise mechanical stability of a structure as well as possibly degrade performance. Some regions with structural damage may not be directly optically visible because physical cracks may not have developed yet. Such notionally 'invisible' damaged regions are locations where material density, composition, or other material physical properties have become modified slightly compared to regions without damage (for example, in regions where corrosion may have just begun or nucleated, or regions that are subjected to stresses and loads which may lead to cracks or mechanical failure of the material).

SUMMARY

In some examples, a method of identifying characteristics of a sample is described that generally comprises coupling a current to a sample such that a magnetic field is generated across a surface of the sample, and the magnetic field varies due to characteristics of the sample. The method also may comprise providing a linearly polarized light to a magneto-optic film that is positioned substantially adjacent the surface of the sample and at least a portion of the linearly polarized light can be reflected by the magneto-optic film as reflected light. The method can further comprise capturing an image of the sample using magneto-optical imaging (MOI) of at least a portion of the reflected light. A plane of the reflected light is rotated with respect to the linearly polarized light due to presence of the magnetic field at a location of the sample where the linearly polarized light is reflected by the magneto-optic film.

In another example, a method of identifying characteristics of a sample is described that generally comprises providing a linearly polarized light to a magneto-optic film. The magneto-optic film can be arranged substantially adjacent to the surface of a sample and the magneto-optic film is effective to reflect at least a portion of the linearly polarized light as reflected light. The method may also comprise coupling a first current through the sample in a first direction to generate a first magnetic field across a surface of the sample, and characteristics of the first magnetic field vary due to characteristics of the sample. The method may also comprise capturing a first set of images of the sample using magneto-optical imaging (MOI) of at least a portion of the reflected light based on the first magnetic field. A plane of the linearly polarized light can be rotated in the presence of the first magnetic field due to the current at a location of the sample where the linearly polarized light is reflected by the magneto-optic film, for example. The method may also comprise summing the first set of images to form a first image output. The method may further comprise coupling a second current through the sample in a second direction to generate a second magnetic field across a surface of the sample, and characteristics of the second magnetic field vary due to characteristics of the sample. The method may also comprise capturing a second set of images of the sample using magneto-optical imaging (MOI) of at least a portion of the reflected light based on the second magnetic field. A plane of the linearly polarized light can be rotated in the presence of the second magnetic field at a location of the sample where the linearly polarized light is reflected by the magneto-optic film. Following, the method may comprise summing the second set of images to form a second image output, and determining a differential image as a difference between the first image output and the second image output.

In still another example, a system for identifying characteristics of a sample is generally described. The system can comprise a power supply configured to couple a direct current (DC) or an alternating current (AC) to the sample to generate a magnetic field across a surface of the sample, and characteristics of the magnetic field vary due to characteristics of the sample. The system, which can operate in either a DC or AC mode, can also comprise a magneto-optic film arranged substantially adjacent the surface of the sample, and a sample analyzer configured to provide a linearly polarized light to the magneto-optic film. At least a portion of the linearly polarized light can be reflected by the magneto-optic film as reflected light, and a plane of the reflected light is rotated with respect to the linearly polarized light due to presence of the magnetic field at a location of the sample where the linearly polarized light is reflected by the magneto-optic film. The system can also comprise an image capture device configured to capture an image of the sample using magneto-optical imaging (MOI) of at least a portion of the reflected light.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
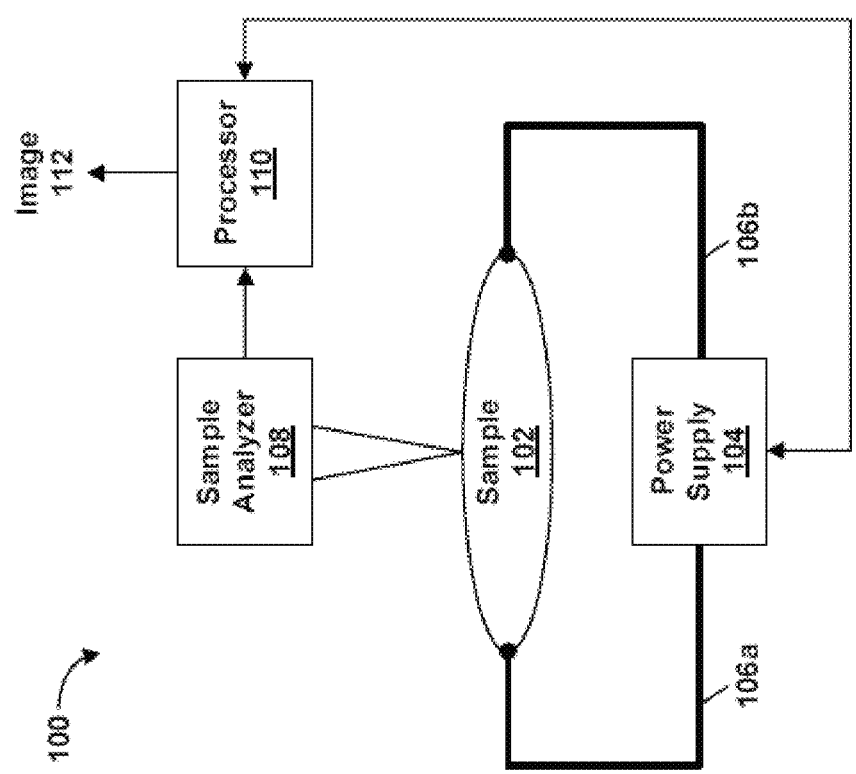
FIG. 1 is an example system for non-destructive evaluation of a sample.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Example embodiments below describe a system and method for non-destructive evaluation of regions of material. Example embodiments include a system that may function in two modes. In a first mode, or DC mode of operation, the system may be configured to directly image regions of material where weak structural damage has occurred (rather than indirectly infer a location). For example, the system may be configured to image a self magnetic field generated by a small DC electric current coupled through the material. In second mode of operation, or AC mode of operation, the system may be adapted to function as an eddy current imager to image areas of material where structural damage may be present.

Using various embodiments described herein, inspection and mapping of damaged regions in complex geometries can be performed using a portable system. Example systems may be configured to identify possible regions of weak damage in material that are likely to develop cracks in the future. The system may use magneto-optical imaging techniques (MOI) to minimally perturb a sample being measured and to map channels of current flow in the material while a current is driven through the system.

Referring now to the figures, FIG. 1 is an example system 100 for non-destructive evaluation of a sample 102, arranged in accordance with at least some embodiments described herein. In some examples, system 100 may include one or more functional or physical components such as a power supply 104, a sample analyzer 108 and/or a processor 110. One or more of the described functions may be divided up into additional functional or physical components, or combined into fewer functional or physical components. In some further examples, additional functional and/or physical components may be added to the examples illustrated by FIG. 1.

A current supplied by the power supply 104 can be coupled to/through the sample 102 using leads 106a-b. The power supply 104 may be configured to provide a direct current (DC), an alternating current (AC), or both. The sample 102 may be any type of material that that may be electrically conductive (or minimally conductive), for example, and does not require any pre-treatment prior to analyzing the sample 102. The sample 102 may be include a coating (e.g., paint), and in such instances, the leads 106a-b may electrically contact an underlying surface through the coating to allow electric current to flow to the sample.

The sample analyzer 108 can be configured to measure or detect characteristics of a magnetic field that is generated by the current coupled to/through the sample 102. Example characteristics of the magnetic field that can be measured or detected by the sample analyzer 108 include a presence of the magnetic field, a strength of the magnetic field, and changes in strength of the magnetic field.

The processor 110 can be configured to receive outputs from the sample analyzer 108 and may also be configured to control the power supply 104 such that the current to can be selectively provided to the sample 102. The processor 110 can also be configured to generate an image 112 using the magnetic field that indicates regions in the sample 102 where defects or structural damage may be present. The image 112 may be displayed on a display (not shown). A display may be incorporated within the sample analyzer 108 or the processor 110, for example.

Components of the system 100 may be combined, for example, the processor 110 may be combined with the power supply 104, which may be coupled to a platform on which the sample 102 can be placed. In addition, the sample analyzer 108 may also be included within or combined with the processor 110 and/or the power supply 104, such that the system 100 can be portable and may be positioned so that the sample analyzer 108 is adjacent to an area on the sample 102 for imaging, for example. Other components may also be included within the system 100.

Locations in the sample 102 that have undergone structural damage may exhibit increased electrical resistance to a flow of electric current compared to other undamaged regions of the sample 102. Thus, electric current will avoid such higher resistance locations with damage compared to lower resistance in the undamaged regions. This may result in a redistribution of current paths around the damage region. As a result, the distribution of a self magnetic field generated from the distribution of current paths over a surface of the sample 102 may change in the vicinity of the damage, for example. The processor 110 may be adapted to receive outputs from the sample analyzer 108 and may be configured to generate a spatial map identifying the distribution of self magnetic fields generated from currents, which can enables mapping of locations with structural damage in the sample 102.

The system 100 in FIG. 1 may be used in multiple modes. For example, the power supply 104 may be configured to provide a direct current (DC) to the sample 102 so that the system 100 operates in a DC mode. Alternatively, the power supply 104 may be configured to provide an alternating current (AC) to the sample 102 so that the system 100 operates in an AC mode or eddy current mode. One or both modes of imaging may be used to characterize and map locations with structural defects and damage in the sample 102 or within a surface of the sample 102.

Figure 2:
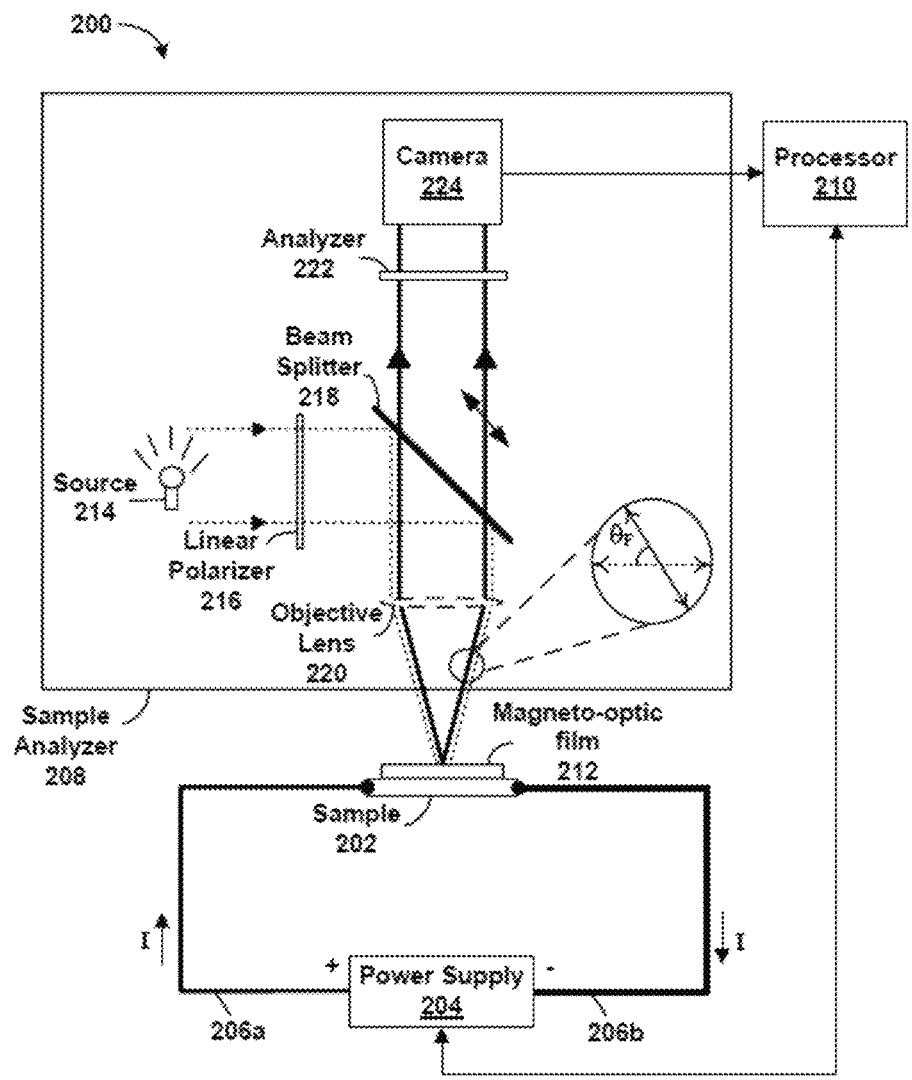
FIG. 2 is an example system that illustrates use of the system in a DC mode.

FIG. 2 is an example system 200 that illustrates use of the system 200 in a DC mode, arranged in accordance with at least some embodiments described herein. In some examples, system 200 may include one or more functional or physical components such as a power supply 204, a sample analyzer 208, a processor 210, a magneto-optic film 212, a light source 214, a linear polarizer 216, a beam splitter 218, an objective lens 220, an analyzer 222, and an image capture device 224. One or more of the described functions may be divided up into additional functional or physical components, or combined into fewer functional or physical components. In some further examples, additional functional and/or physical components may be added to the examples illustrated by FIG. 2. The system 200 may be a portable, hand-held station, for example.

The system 200 can be used to image a magnetic field generated by a DC current coupled through a sample 202. The DC current can be provided by the power supply 204 that is coupled to electrical contacts (e.g., pins) on a surface of the sample 202 using leads 206a-b.

The sample analyzer 208 can be placed adjacent or substantially adjacent the sample 202 (e.g., the analyzer 208 may be placed approximately at a distance of about 2 cm from the sample 202, and the magneto-optic film may be positioned at a distance of less than about 0.5 microns from a surface of the sample 202 during measurements), and can be coupled to the processor 210. The sample analyzer 208 can be configured to measure or detect characteristics of a magnetic field that is generated by the current coupled to/through the sample 202. Example characteristics of the magnetic field that can be measured or detected by the sample analyzer 208 include a presence of the magnetic field, a strength of the magnetic field, and changes in strength of the magnetic field.

The processor 210 can be configured to receive outputs from the sample analyzer 208 and may also be configured to control the power supply 204 such that the current to can be selectively provided to the sample 202. The processor 210 may be configured to output an image that can indicate structural damage or defects in the surface of the sample 202.

The magneto-optical film 212 may be placed over or adjacent the sample 202 during measurements. The sample analyzer 208 may include a window comprising the magneto-optical film 212 which may be placed (or pressed) in contact with a surface of the sample 202, or placed substantially adjacent the sample 202. Alternatively, the magneto-optical film 212 may be separate from the sample analyzer 208 and may be placed near or directly onto a surface of the sample 202 to be analyzed.

In other examples, the sample analyzer 208 may include a spring loaded detachable mount that can be adapted to hold magneto-optic films of different sizes, and which can be employed for a pressure contact of the magneto-optic film 212 with the surface being imaged.

The sample analyzer 208 can include the light source 214 (e.g., LED, light bulb, etc.). The source 214 may also be about a 100 watt, mercury vapour lamp followed by a filter that is configured to filter the white light to produce a light of wavelength of about 550 min (green light), for example. The light source 214 may be configured to output light which can be passed through the linear polarizer 216 and can be reflected by the beam splitter 218 to reach the objective lens 220. The objective lens 220 can be configured to focus the light onto the magneto-optic film 212, and may be a strain free objective lens, which may help to optically magnify a size of a portion of the sample 202 that is being imaged and tested. The objective lens 220 may be capable of any number of different magnifications, such as about 2.5×, 10×, 20× or 50×, for example.

Light can be reflected by the magneto-optic film 212 and can pass back through the objective lens 220 and through the beam splitter 218 to the analyzer 222. Light that passes through the analyzer 222 can be received at the image capture device 224. The image capture device 224 can be configured to output to the processor 210 for further processing of the image, for example.

The image capture device 224 may be a charge-coupled device (CCD) that has 512×512 pixels or is approximately a 2.6 megapixel image capture device, for example. The image capture device 224 may contain a silicon-based semiconductor chip with a two-dimensional matrix of photosensors or pixels. The photosensitive pixels can convert incoming light into an electrical signal. In the image capture device 224, an electrical signal from each pixel can be digitized and converted to a gray scale value when the electrical signal from each pixel is converted into a picture. The image capture device 224 can be a 12 or 16 bit image capture device (e.g., to display $2^{12}$ or $2^{16}$ shades of gray), for example. The image capture device 224 may have high quantum efficiency to measure percentages of incoming light converted into an electronic signal of more than about 50% at a wavelength of about 550 nanometers, for example.

Figure 3:
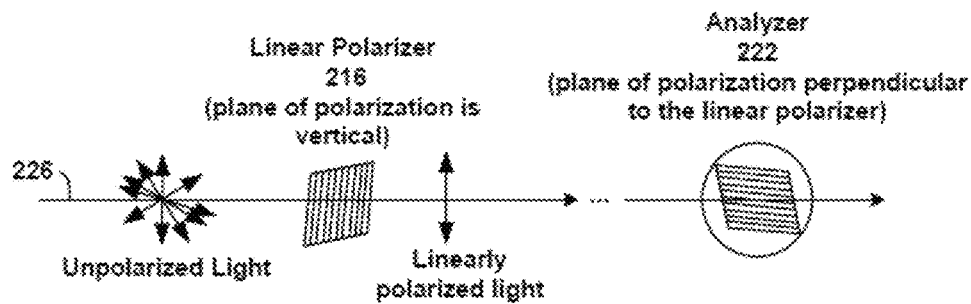
FIG. 3 illustrates portions of the system of FIG. 2 including a linear polarizer and an analyzer.

FIG. 3 illustrates portions of the system 200 including the linear polarizer 216 and the analyzer 222, arranged in accordance with at least some embodiments described herein. The linear polarizer 216 is configured to receive a light beam 226 of unpolarized light and transmit light uniformly vibrating in a single plane while absorbing vibrations along an orthogonal plane. The linear polarizer 216 may be a polymer based film (e.g., Polaroid film). When unpolarized light is incident on the linear polarizer 216, emerging light is linearly polarized.

The analyzer 222 is also a film linear polarizer, however, film of the analyzer 222 can be mounted on a circular holder that can be configured to rotate about an axis through a center of the circular holder. By rotating the holder, a plane of polarization of the analyzer 222 can be made to be perpendicular to the plane of polarization of the linear polarizer 216. The plane of polarization of the linear polarizer 216 and the analyzer 222 may be kept to be mutually perpendicular, for example. Little or no output of light (or nearly zero intensity) is achieved output from the analyzer 222 if incoming incident light on the analyzer 222 is polarized in a plane perpendicular to the analyzer 222.

Using the system 200 in FIG. 2, a spatial distribution of electric current paths over a metal surface can be imaged. To image paths taken by electric current coupled through the sample 202, the magnetic field generated by the DC electric currents is imaged. The magnetic field may be referred to as the self-magnetic field. For example, a distribution of electric current paths in the sample creates a distribution of a self-magnetic field ($B_z(x,y)$) across a surface of the sample 202. The distribution of the self-magnetic field $B_z(x,y)$ implies a distribution of Faraday rotation intensities ($I(x,y)$) at different locations of the sample 202. Capturing the spatial intensity distribution, $I(x,y)$, with MOI yields information about the self-magnetic field distribution $B_z(x,y)$, which in turn yields information about how the current paths are distributed across the sample 202.

Certain materials rotate a plane of a linearly polarized light passing through them in the presence of a magnetic field. This phenomenon is known as the Faraday Effect. FIG. 2 illustrates one example. The light source 214, which may be an incoherent light source of wavelength of about 550 nanometers, can be linearly polarized using the linear polarizer 216. Incident linear polarized light can be reflected by a surface of the magneto-optic film 212 that is positioned adjacent a surface of the sample 202 being inspected. The magneto-optic film 212 may be a Bismuth doped yttrium-iron-garnet single crystal film (Bi:YIG). Such magneto-optic films are materials that produce Faraday rotations in the presence of small magnetic fields. The magneto-optic film 212 effectively rotates the plane of polarization of the incident light beam by an amount ($\theta_F$) proportional to a local magnetic field ($B_z$) present at a location of the sample 202 where the light is reflected. The reflected light passes through the analyzer 222 into the image capture device 224.

Generally, the portion of the light which is Faraday rotated passes through the analyzer 222; however, in practice small amounts of light that is substantially Faraday rotated may pass through the analyzer 222 as well. For example, referring back to FIG. 3, a plane of polarization of the analyzer 222 can be made to be perpendicular to the plane of polarization of the linear polarizer 216 so that little or no output of light (or zero intensity) is achieved output from the analyzer 222 if incoming incident light on the analyzer 222 is polarized in a plane perpendicular to the analyzer 222. Thus, without the light being rotated by the magneto-optic film 212, to offset the light being rotated by the linear polarizer 216, no light would be received at the image capture device 224. Thus, incident light can be rotated by the magneto-optic film 212 due to a local magnetic field ($B_z$) present at a location of the sample 202 where the light is reflected passes through the analyzer 222 into the image capture device 224.

Figure 4:
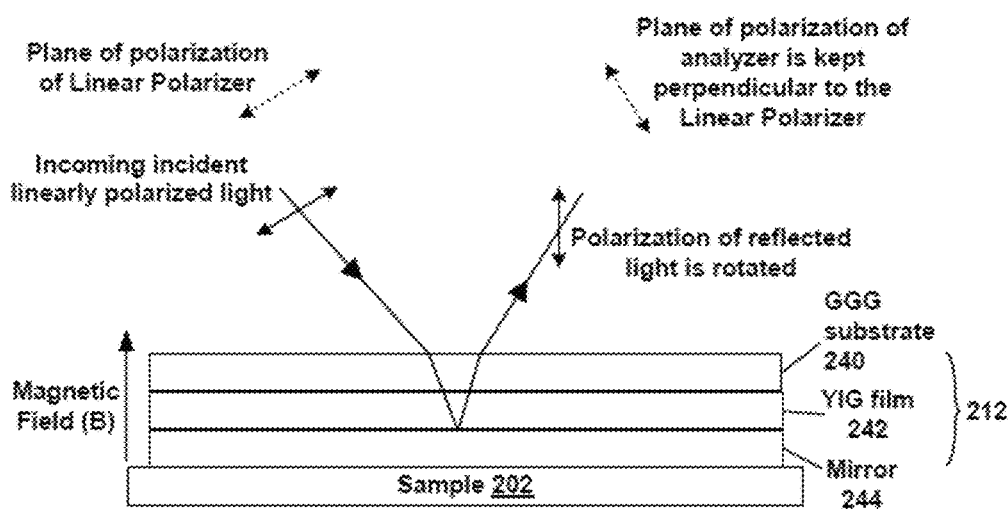
FIG. 4 is an example illustration of a magneto-optic film and a sample.

FIG. 4 is an example illustration of the magneto-optic film 212 and the sample 202, arranged in accordance with at least some embodiments described herein. The magneto-optic film 212 is shown to be in contact with the sample 202, however, the magneto-optic film 212 and the sample 202 may not be contacting during testing. The magneto-optic film 212 may be a Bi-doped yttrium iron garnet film (YIG) 242 grown on a gallium-gadolinium-garnet (GGG) substrate layer 240. Below the YIG film 242 is a reflecting mirror layer of aluminum 244. The magneto-optic film 212 may include other layers as well.

As shown in FIG. 4, linearly polarized light is incident on the magneto-optic film 212 and is reflected by the magneto-optic film 212. On each pass of the polarized light through the magneto-optic film 212, the initial polarization can be rotated in a direction determined by an applied magnetic field (B) (which is emitted from the sample 202). By using the mirror 244, a double pass geometry can be achieved in which light traverses the layers twice, and thereby a rotational sensitivity is enhanced by a factor of two, for example. In other embodiments, the mirror 244 layer may be omitted.

The YIG film 242 may have a thickness (d) (e.g., such as about 6 micrometers) and is deposited on or coupled to the GGG substrate layer 240. The magneto-optic film can be placed in close proximity to the sample whose magnetic-field $B_z(x,y)$ is being mapped. A light beam may not directly interact or contact a surface of the sample 202 due to the mirror 244 on the YIG film 242. Thus, the light beam may be reflected by the mirror 244 as shown in FIG. 4, for example. However, a plane of the linearly polarized light can be rotated in the presence of the magnetic field at a location of the sample 202 where the linearly polarized light can be reflected by the mirror 244, for example.

Thus, the incoming incident light can be reflected in the direction determined by an applied magnetic field (B), and this reflected light will be able to pass through the analyzer 222 of FIG. 2 which has a plane of polarization perpendicular to the linear polarizer 216, for example.

Figure 5:
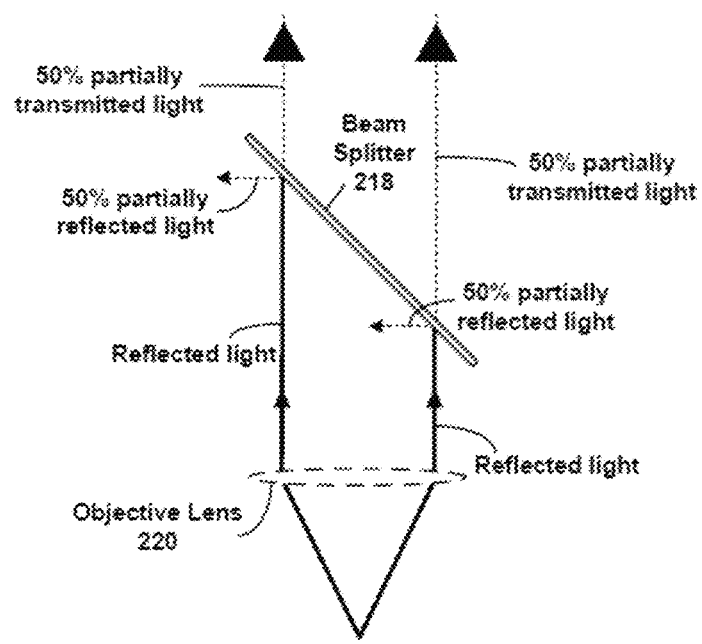
FIG. 5 illustrates a portion of the example system of FIG. 2.

FIG. 5 illustrates a portion of the example system 200 in FIG. 2, in accordance with at least some embodiments described herein. The beam splitter 218 may be a partially silvered mirror surface, which has about 50% reflectance and about 50% transmittance of incident light. As a result of the partial transmittance, a portion of light may be partially reflected at the beam splitter 218, and a portion of the light may be transmitted to the image capture device (not shown). The light used may be of sufficiently high intensity so that the light transmitted to the image capture device is sufficient for imaging purposes.

Thus, in one embodiment, about 50% of light reflected by the material being tested reaches the image capture device through the beam splitter 218. In other embodiments, depending on materials used for the beam splitter 218, more or less than 50% of light may reach the image capture device. Thus, based on desired intensities of light to reach the image capture device, materials for the beam splitter 218 can be selected accordingly.

Referring back to FIG. 2, an intensity distribution of a rotated polarized beam of light (I(x,y)) after the analyzer ($I(x,y) \propto [B_z(x,y)]^2$) is captured by the image capture device 224 (e.g., with high quantum efficiency, such as about 50% at 550 nanometers), which enables a direct two dimensional visualization of the local field distribution ($B_z(x,y)$) across the surface of the sample 202.

The magneto-optical film 212 used for imaging can be configured in sizes of about a multiple millimeters (mm) by multiple millimeters from a wafer of indicator film of a diameter of about a multiple inches by a multiple inches. A small surface area of the magneto-optical film 212 sets an upper limit on a maximum area that can be magneto-optically imaged to be about a multiple millimeters by multiple millimeters, for example. However, the magneto-optic film 212 may be cut to smaller or larger dimensions, namely, multiple centimeters by multiple centimeters to achieve a larger field of view for magneto-optical imaging (along with using lower magnification lenses), for example. Using a larger area magneto-optical material and increasing a field of view of the system 200 enables detection of larger sized defects (e.g., sizes in the range of about a few centimeters) as well as small defects (ranging in size from few mm down to a few microns). Thus, low and high magnification lenses may be used to enable magneto-optical imaging of features by zooming from features of a few centimeters in size down to few micron scale sized features.

The image capture device 224 that captures the Faraday rotated light intensity can be interfaced with the processor 210, which may also be simultaneously interfaced with the power supply 204. The processor 210 can be configured to trigger the power supply 204 to send DC electric current through the sample 202 and the image capture device 224 can also be simultaneously triggered (or triggered at approximately the same time) by the processor 210 to begin capturing MOI images of light intensities altered by the self-magnetic field distribution generated by the flowing electric current. Information on the current paths taken by the currents revealed via the MOI self-magnetic field images can be used to map local regions on the surface (or subsurface) that have structural damage.

Figure 6:
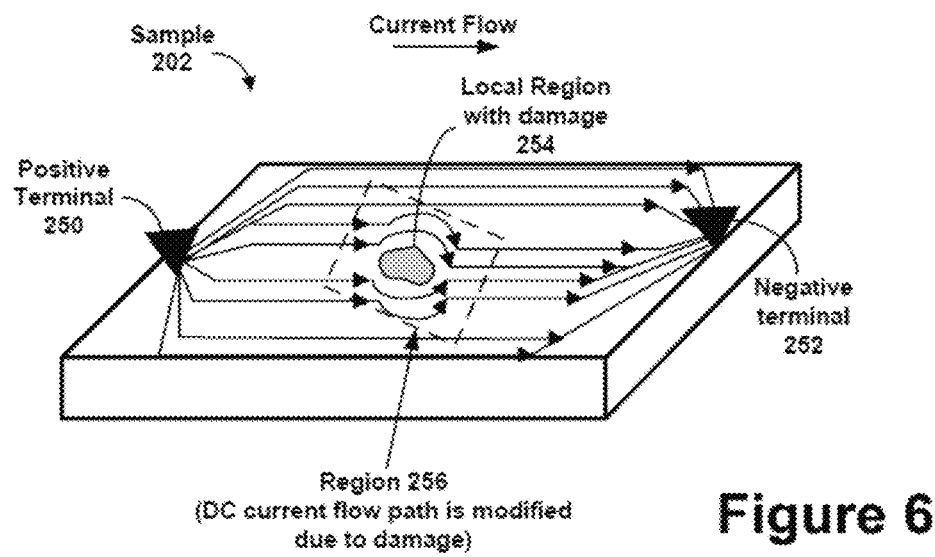
FIG. 6 is a conceptual diagram illustrating current paths on a surface of a sample.

FIG. 6 is a conceptual diagram illustrating current paths on a surface of the sample 202, in accordance with at least some embodiments described herein. For example, DC current may be coupled to the sample 202 at a positive terminal 250, traverse across a surface of the sample 202, and exit at a negative terminal 252. Regions in the surface of the sample 202 that have structural damage may locally possess an electric resistance characteristics that is higher than metal. For example, region 254 (shown shaded in FIG. 6) may have some type of structural damage and will offer a higher electrical resistance to the DC current. In this example, the region 254 with damage may have dimensions of about 0.5 micrometers ($10^{-6}$ meters) or greater. The higher electrical resistance is due to the fact that the region 254 with damage might possess micro-cracks, defects or varying density and composition (due to fatigue loads, oxidation, moisture or chemical related corrosion, etc).

The local higher resistance can lead to modification in the electric current paths flowing across the metal surface as electric currents take the least resistance path. A change in the electric current path in the vicinity of the region (or in region 256) with fatigue due to neighbouring regions devoid of fatigue changes the self-magnetic field distribution in the vicinity of the region 256 with structural damage. A modified self-magnetic field in the vicinity of the region 256 with damage is imaged with to map regions of damage in the sample 202.

Using the positive and negative terminals 250 and 252, a DC current can be driven in a specified and predefined direction through the material, and a strength of the current is also predefined and controlled. Thus, ambiguities relating to interpreting information from self-magnetic field MOI images and mapping of regions with structural damage may be removed, in one example.

A depth of imaging depends on a strength of a magnetic field generated by currents flowing at a particular depth in the material. Since a magnetic field sensitive element (e.g., magneto-optic indicator film) is located at the surface of the material being imaged, film is sensitive to fields generated from currents flowing up to a depth of about a few microns beneath the surface of the material. For greater depth sensitivity, larger probing currents can be sent through the material so that larger currents are flowing at larger depths inside the material.

In some embodiments, the DC electric current that is coupled through the sample 202 may be on the order of about tens of amperes. Large currents (e.g., about 10 Amps) generate strong self-magnetic fields (e.g., on the order of a few tens of gauss) that are distributed over the surface of the sample 202 where the currents are distributed. Large self-magnetic fields can be imaged with embodiments using the MOI techniques, which may provide a depth sensitivity of about a few 100 microns below the material's surface. The strong fields present at the surface from the large currents flowing deep inside the surface of the material would be imaged by the magneto-optical material on the surface of the material. Large currents may, however, have drawbacks, such as heating effects in the metal causing thermal stresses that affect and may modify the region of damage that is being mapped. In addition, using large electric current may make distinguishing regions which have minor damage (small variations in electrical conductance as compared to neighbouring regions without damage) difficult to locate. For example, in many instances, regions that are on the brink of developing cracks may possess a small change in local electric resistance compared to regions without damage.

In the undamaged regions of the metal surface, the self-magnetic field signal can be so large, for example, such that minor variations in the self-magnetic field due to modified current paths in the vicinity of the region with slight damage may not be noticed by the system 200 (e.g., due to large background self-magnetic field signals).

In other embodiments, to be able to sensitively probe regions of slight damage, small DC electric currents may be used so that any background self-magnetic field signals from undamaged regions remains small. Small DC electric currents on the order of a few milli ($10^{-3}$) amperes may be used (e.g., about 1 mA to about 100 mA), for example, and a depth sensitivity can be up to about a few tens of microns below the surface of the sample. In addition to, or rather than detecting local variations in the strength of DC current, the system 200 may sensitively detect light contrast variations in an image to detect variations in the current flow paths thereby enabling identification of regions with structural damage in materials. The system 200 may be used to investigate a diverse variety of materials for damage.

For depth sensitive imaging, initially, imaging may be performed using small DC currents to search for defects/damages occurring within a depth of about a few tens of microns from the surface of the material. The DC current can be gradually increased so that the sensitivity to image information at different depths in the material is achieved, for example.

Thus, in one example, in the DC mode of operation, small changes in the current path can be detected to identify small changes in local properties of the sample due to an onset of weak structural changes or an onset of structural damage that may evolve into physical damages such as cracks. In one example, the system 200 can be configured with sufficient spatial resolution to detect regions of fatigue or cracks that have sizes ranging from about a few millimeters (or centimeters using larger area magneto-optical indicator films) to about half a micrometer range.

Little or no surface preparation is required to place the magneto-optic film 212 near or on a surface of the material to be imaged. In instances in which surface conditions of the material include contaminants or imperfections that may not directly be a micro-crack, dislocation in grain structure, or other type of damage, false positives for defects may arise. However, the system 200 functions as a high magnification polarizing optical microscope in the absence of the magneto-optic film 212. As a result, with high magnification optical microscopy, imperfections on the material's surface can be identified through optical inspection with the microscope arrangement of the system 200. Furthermore, crystalline defects in a material (e.g., such as edge dislocations or twin boundaries) produce birefringent effects that affect polarization of light. Therefore, the system 200 without the magneto-optic film 212 may detect such defects in a material.

In addition, cracks can be further identified or verified by comparing similarities and differences between magneto-optical images obtained from a region and magneto-optical images obtained from neighbouring regions. Unlike cracks, naturally occurring or imperfections on the surface of a material would likely occur elsewhere on the material's surface. By comparison of a magneto-optical images around the region of interest with those from the region of interest, feature observed in the magneto-optical images can be discerned as due to damages, for examples.

Furthermore, a change in a current path due to a crack or damage is stronger than what may be observed due to imperfections on the surface. Thus, differences in contrasts in a magneto-optical image may be stronger due to a crack than due to an imperfection on the metal surface, for example.

Referring back to FIG. 2, in operation, in one embodiment, magneto-optical images can be captured by the image capture device 224 with DC currents driven through the material, and averaged over a number of captured images.

Figure 7:
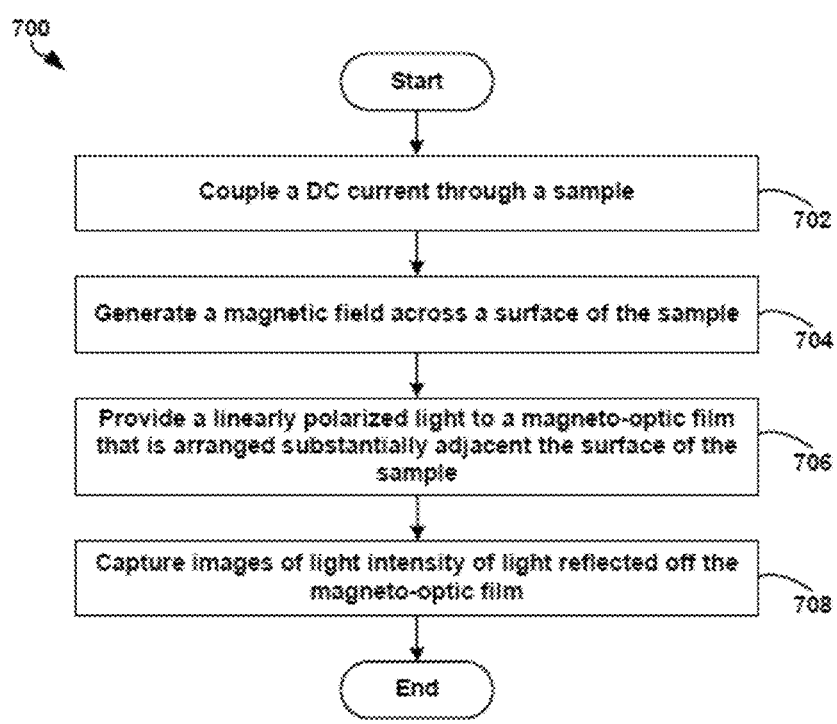
FIG. 7 shows a flowchart of an illustrative embodiment of a method for imaging characteristics of a sample.

FIG. 7 shows a flowchart of an illustrative embodiment of a method 700 for imaging characteristics of a sample (e.g., such as generating magneto-optical images of a sample), in accordance with at least some embodiments described herein. It should be understood that for this and other processes and methods disclosed herein, the flowchart shows functionality and operation of one possible implementation of present embodiments. In this regard, each block may represent a module, a segment, or a portion of program code, which includes one or more instructions executable by a processor for implementing specific logical functions or steps in the process. The program code may be stored on any type of computer readable medium, for example, such as a storage device including a disk or hard drive. The computer readable medium may include non-transitory computer readable medium, for example, such as computer-readable media that stores data for short periods of time like register memory, processor cache and Random Access Memory (RAM). The computer readable medium may also include non-transitory media, such as secondary or persistent long term storage, like read only memory (ROM), optical or magnetic disks, compact-disc read only memory (CD-ROM), for example. The computer readable media may also be any other volatile or non-volatile storage systems. The computer readable medium may be considered a computer readable storage medium, for example, or a tangible storage device.

In addition, each block in FIG. 7 may represent circuitry that is wired to perform the specific logical functions in the process. Alternative implementations are included within the scope of the example embodiments of the present disclosure in which functions may be executed out of order from that shown or discussed, including substantially concurrent or in reverse order, depending on the functionality involved, as would be understood by those reasonably skilled in the art.

Method 700 may include one or more operations, functions or actions as illustrated by one or more of blocks 702, 704, 706, and/or 708. Although the blocks are illustrated in a sequential order, these blocks may also be performed in parallel, and/or in a different order than those described herein. Also, the various blocks may be combined into fewer blocks, divided into additional blocks, and/or eliminated based upon the desired implementation.

Processing for method 700 may begin at block 702, "Couple a DC current through a sample." Block 702 may be followed by block 704, "Generate a Magnetic Field Across a Surface of the Sample." Block 704 may be followed by block 706, "Provide a linearly polarized light to a magneto-optic film that is arranged substantially adjacent the surface of the sample." Block 706 may be followed by block 708, "Capture images of light intensity of light reflected off the magneto-optic film."

Initially, as shown at block 702, a DC current is coupled through a sample. For example, DC current may be coupled through a sample in a predefined and controlled direction using a positive and negative terminal on the sample. In regions where the sample has a damage (e.g., a crack), resistance in those regions will be larger than in regions with no damage. Thus, as the DC current flows through the material, the DC current will flow through areas of lowest resistance. As a result, the DC current will couple through areas of no damage and avoid areas that have defects. The DC current will bend around regions of defects, for example.

As shown at block 704, after injection of DC current into the sample, a magnetic field is generated across a surface of the sample based on the direct current. As shown at block 706, a linearly polarized light can be provided to a magneto-optic film, which is arranged substantially adjacent the surface of the sample and the linearly polarized light will be reflected by the magneto-optic film.

Following, as shown at block 708, images are captured of light intensity of light reflected by the magneto-optic film. For example, a plane of the linearly polarized light is rotated in the presence of the magnetic field at a location of the sample where the linearly polarized light is reflected by the magneto-optic film. The rotated linearly polarized light can be provided through an element that passes (or substantially passes) light of a particular polarization so as to allow the rotated linearly polarized light to be captured in images by an image capture device, for example.

Thus, images of MOI techniques may be used to measure $B_z(x,y)$ by imaging the Faraday rotated ($\theta_F = 2VdB_z$) linearly polarized light intensity ($I(O_F) \propto B_z^2$). Successive MOI images can be captured synchronously at a frame rate of about one frame per second (fps), or faster such as at about 30 fps to about 100 fps, for example. Images may be averaged over a number of images to obtain a result.

In an instance in which the sample includes a non-planar surface, the non-planar surface can be constructed approximately as a sum of smaller planar surfaces. By magneto-optical imaging the small planar regions making up an irregular surface and combining all such images, a magneto-optical image or map of the irregular surface can be constructed, for example. Furthermore, at areas in which defects are identified on a surface, the system may optionally include a laser to mark the location, for example.

In another embodiment, magneto-optical images can be captured by the image capture device 224 with DC currents driven through the material in a first direction, and then magneto-optical images can be captured with DC currents (of same strength as current driven in the first direction) sent through the material in a second direction reverse to the first direction. A magnitude of the DC currents may be small, such as on the order of a few milli ($10^{-3}$) amperes, for example. A difference between the two sets of magneto-optical images obtained from two opposite current directions can then be calculated resulting in a difference image. The final differential image can be obtained by averaging over a number of difference images captured, for example.

Figure 8:
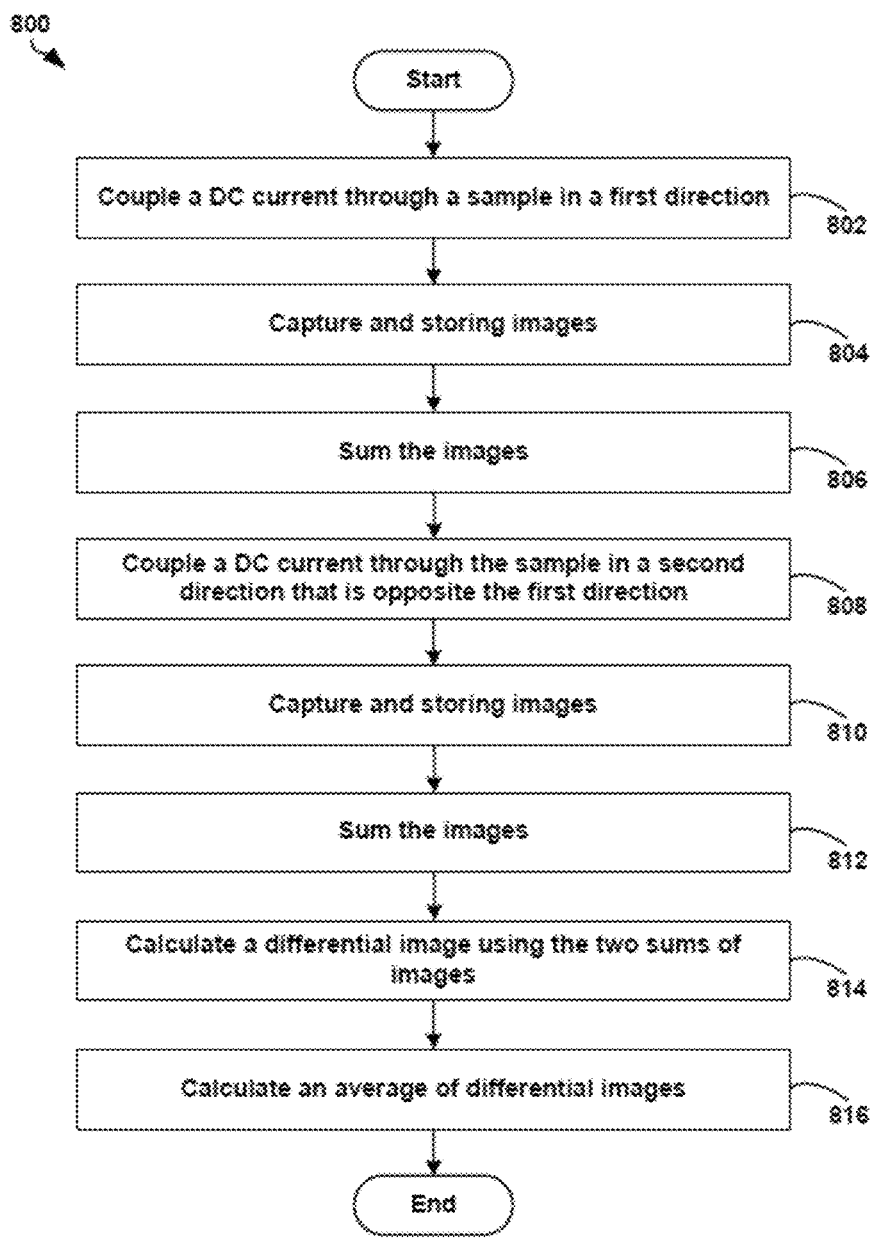
FIG. 8 shows a flowchart of an illustrative embodiment of another method for imaging characteristics of a sample.

FIG. 8 shows a flowchart of an illustrative embodiment of another method 800 for imaging characteristics of a sample (e.g., such as generating magneto-optical images of a sample), in accordance with at least some embodiments described herein. Method 800 may include one or more operations, functions or actions as illustrated by one or more of blocks 802, 804, 806, 808, 810, 812, 814, and/or 816. Although the blocks are illustrated in a sequential order, these blocks may be performed in a different order than those described herein. Also, the various blocks may be combined into fewer blocks, divided into additional blocks, and/or eliminated based upon the desired implementation.

Processing for method 800 may begin at block 802, "Couple a DC current through a sample in a first direction." Block 802 may be followed by block 804, "Capture and store images." Block 804 may be followed by block 806, "Sum the images." Block 806 may be followed by block 808, "Couple a DC current through the sample in a second direction that is opposite the first direction." Block 808 may be followed by block 810, "Capture and storing images." Block 810 may be followed by block 812, "Sum the images". Block 812 may be followed by block 814, "Calculate a differential image using the two sums of images". Block 814 may be followed by block 816, "Calculate an average of differential images".

Initially, a DC current is coupled through a sample in a first direction, as shown at block 802. After injection of the DC current into the sample, a magnetic field is generated across a surface of the sample based on the direct current, and a linearly polarized light can be provided to a magneto-optic film that is arranged substantially adjacent the surface of the sample and the linearly polarized light will be reflected by the magneto-optic film, for example.

Next, as shown at block 804, m images of light intensity are captured and stored. Images can be captured of light intensity of light reflected by the magneto-optic film. Following, the m images are summed together, at block 806. For example, after each subsequent image is captured, the image may be added to a previously captured image, and the sum of the two images can be rewritten at the same location in memory where the first image was stored. The sum of images may be considered to be a sum of effects of current coupled through the sample (e.g., $$\sum_{i=1}^{m} I_i^+).$$

Next, a direction of the DC current is reversed with respect to the first direction, while keeping a strength of the DC current the same, and the DC current is coupled through the sample (e.g., in a direction opposite the first direction), as shown at block 808. Again, as shown at blocks 810 and 812, m images are captured, stored, and summed (e.g., $$\sum_{i=1}^{m} I_i^-).$$

A differential image can then calculated, as shown at block 814. The differential image may be obtained as $$\Delta I = \sum_{i=1}^{m} I_i^+ - \sum_{i=1}^{m} I_i^-.$$

Alternatively, a difference between a mean of each of the summed images can be obtained, for example.

The difference image can be averaged over a number of differential images, as shown at block 816. For example, a number of differential images can be obtained by repeating the process in blocks 802-814 to obtain n differential images. The averaged differential image may be $$D = \frac{\sum_{i=1}^{m} \Delta I_i}{(n \times 2m)},$$

and may include high signal-to-noise ratio (SNR) to detect small variations in contrasts of the Faraday rotated light intensity, for example. Small changes in the contrasts of the Faraday rotated light can be used to image changes in the current flow paths.

Figure 9C:
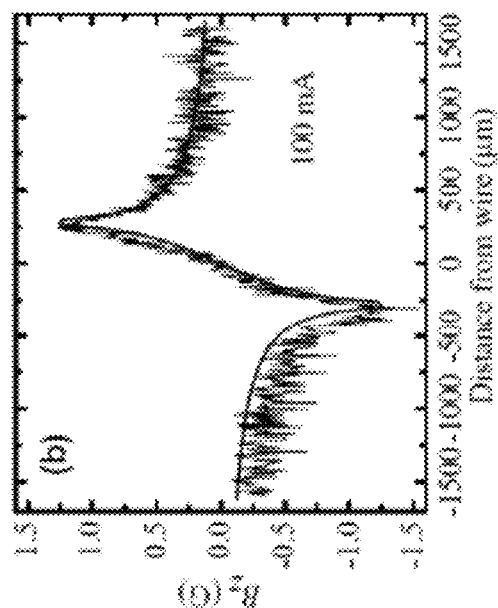
FIGS. 9a-c are illustrations that show an example distribution of a self-magnetic field generated from a current coupling through a film.
Figure 9B:
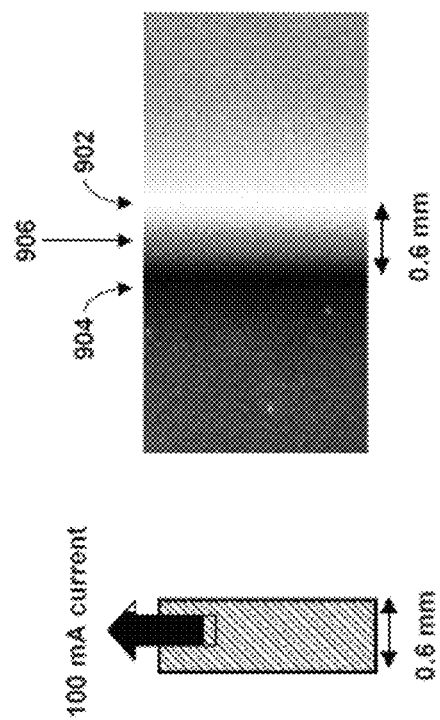
Figure 9A:
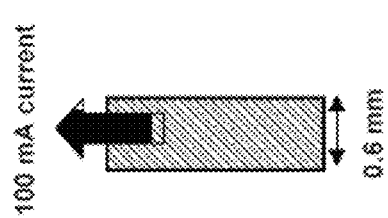

FIGS. 9a-c are example illustrations that show an example distribution of a self-magnetic field generated from a 100 mA current coupled through a thin Aluminium film in an MOI. FIG. 9a illustrates the thin Aluminium film of about 0.6 mm wide through which about a 100 mA current is coupled, in accordance with at least some embodiments described herein.

FIG. 9b illustrates an image of the magneto-optical intensity (I(x,y)) (e.g., intensity of the Faraday rotated light) across the film, in accordance with at least some embodiments described herein. In FIG. 9b, a bright region 902 indicates one edge of the film (e.g., a right edge) and a dark region 904 indicates the other edge of the film (e.g., a left edge) with a gradient 906 in the gray shade traversing from the bright region 902 to the dark region 904 or traversing through the thin film. The bright and dark contrast in the image corresponds to the self-magnetic field generated by the current flowing through the thin film. As mentioned, the brightest and the darkest contrast in the image are obtained across the two edges of the thin Aluminium film. Moving from the bright 902 to the dark region 904, contrasts gradually decay and reach a nominal gray value that corresponds to little or no net self-magnetic field value due to the current flowing inside the film at distances away from the film edges.

FIG. 9c illustrates an example graph of the self-magnetic field distribution across the Aluminium thin film. In the graph, the smooth solid line is a calculation of the self-magnetic field distribution generated by a DC electric current distributed uniformly across the Aluminium thin film (for a straight current carrying strip using Biot-Savart's law), and the other line is a measured or observed value. In this example, there is a closeness of similarity of the calculated $B_z(x)$ behavior with the data obtained using MOI. The bright region 902 on the left edge of the strip is shown in the graph where $B_z$ values are about 1 G, and the dark region 904 on the right edge of the aluminium thin film is shown in the graph where $B_z$ values are about −1 G. For example, bright and dark regions 902 and 904 adjacent to each other near the center of the image in FIG. 9b correspond to maximum values of $\pm B_z$ in the graph of FIG. 9c. On either side of the bright and dark regions 902 and 904, the magnetic fields decay ($\sim 1/r^2$).

Figure 10A:
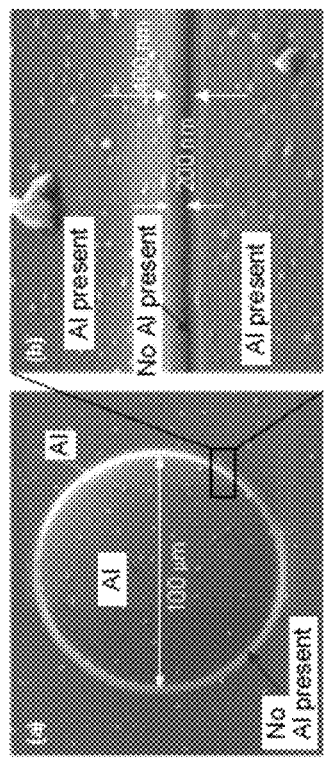
FIGS. 10a-c are illustrations that show another example distribution of a self-magnetic field generated from a current coupling through a film.

To illustrate images of structural damage in the film, an intentionally generated structurally damaged region was produced in the thin film. A structural damage of a circular ring enclosed between two concentric circles was made within the thin film. An outer diameter of the ring is about 100 microns and an inner diameter of the ring is about 99.9 microns. A top layer of the Aluminium thin film surface within the 0.1 micron width ring region between the two concentric circles was damaged using a focussed ion beam milling machine (FIB). FIG. 10a is an example scanning electron microscope image of the damage region produced in the Aluminium film, in accordance with at least some embodiments described herein.

Figure 10C:
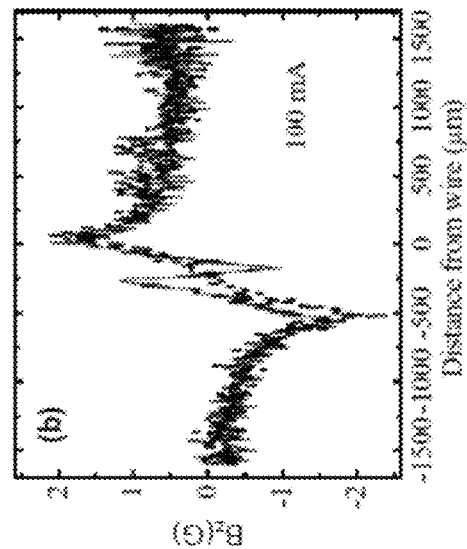
Figure 10B:
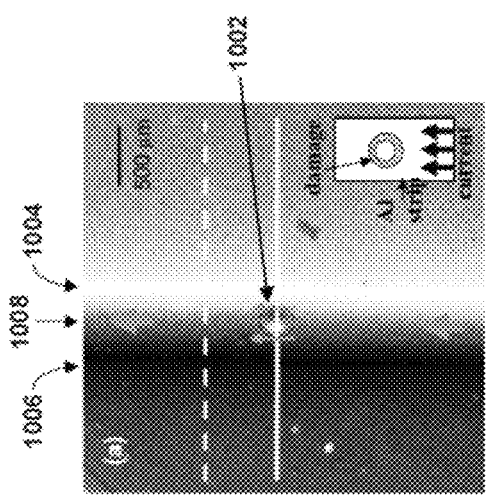

FIGS. 10b-c include illustrations that show an example distribution of a self-magnetic field generated from about a 100 mA current coupling through the thin Aluminium film with the structural damage, in accordance with at least some embodiments described herein. FIG. 10b is an image of the magneto-optical intensity (I(x,y)) across the thin film in the vicinity of the circular damaged region. In the inset of FIG. 10b, the Aluminium strip is shown with the damage and current flow from bottom to top of the film. A self field distribution 1002 around the circular ring region with the damage in the Aluminium film is also shown. The self-field distribution 1002 is the region where current flow has changed due to the defect. In regions of the film away from the defect, there is a light edge 1004, a dark edge 1006, and a gray field 1008 corresponding to the left and right edges of the Aluminium film (of width 0.6 mm), which is similar to the contrast seen of the undamaged thin film in FIG. 9b. Near the defective region, the self field distribution 1002 of the damage area produces another set of dark and bright regions that are observed with a reverse order compared to the bright 1004 and dark regions 1006 at the Aluminium film edges. Thus, the region 1002 with damage can be identified in the image. Further, the image in FIG. 9b can be compared to the image in FIG. 10b to identify differences and to identify the areas that may include damages.

FIG. 10c illustrates an example graph of the self-magnetic field distribution across the Aluminium thin film with the damage. The nature of the self-magnetic field around the damaged region is different from the self-magnetic field distribution in the region away from the damage. The self-magnetic field around the damaged area in is due to a redistribution of current paths around the damaged area that is different from uniformly distributed current paths away from the damaged area. For example, current flow bifurcates into two paths around the region with damage, and then the two paths rejoin into a single uniform flow path away from the region with damage. Each flow path around the damaged region generates a bright contrast on the left and dark contrast on the right. The combination of the sequence of bright and dark contrasts generated by the two bifurcated current paths in the neighbourhood of the damaged region produces the changed sequence of bright and dark contrast in the vicinity of the damage. The magnetic field is shown in the graph in FIG. 10c to have an additional spike of 1 G and −1 G as compared to the graph shown in FIG. 9c. The additional spikes correspond to the two new contrast changes in the image.

A change in current path due to a crack or damage produces a contrast difference in the magneto-optical image that is stronger than what can be produced with an imperfection (not a region with damage) on the metal surface. For example, the Aluminium film may have had imperfections; however, in the magneto-optical image of the self field generated by the current distribution, contrast variations occur due to the change in the path of the current flowing around the region where a defect or damage was created in the aluminium film. Away from the region of the damage in the images, there are no regions where similar contrast changes are substantially present due to imperfections in the film. Imperfections may lead to noise or fluctuations in a magneto-optical signal, but are unlikely to cause major variations in contrast of the image like those created due to damage. However, if imperfections are present and produce significant contrast variations in the magneto-optical image, then such areas are regions that may be further investigated as possible sources for developing cracks or fatigue in the future, for example.

Surface shapes and configurations may also affect the imaging process. Any irregular surface can be constructed approximately as a sum of smaller planar surfaces. If the surface is highly irregular with deformations, then such an irregular surface may be difficult to image. However, if the irregular surface has planar surface regions of an area of about a few millimeters by a few millimeters, then in such a case, the irregular surface can be imaged using a magneto-optical indicator film element with a small area (namely, of about a few mm×few mm). By magneto-optical imaging, the small planar regions comprising the irregular surface and combining all such images, a magneto-optical image or map of the irregular surface can be constructed.

After calculating or generating a magneto-optical image of a surface, regions or areas including structural fatigue/damage can be identified by identifying changes in current flow path or current patterns around a region of the material with structural fatigue/damage as variations in bright and dark contrasts in magneto-optical images. In one example, images of a magnetic-field distribution can be numerically inverted to determine a current distribution.

Figure 11:
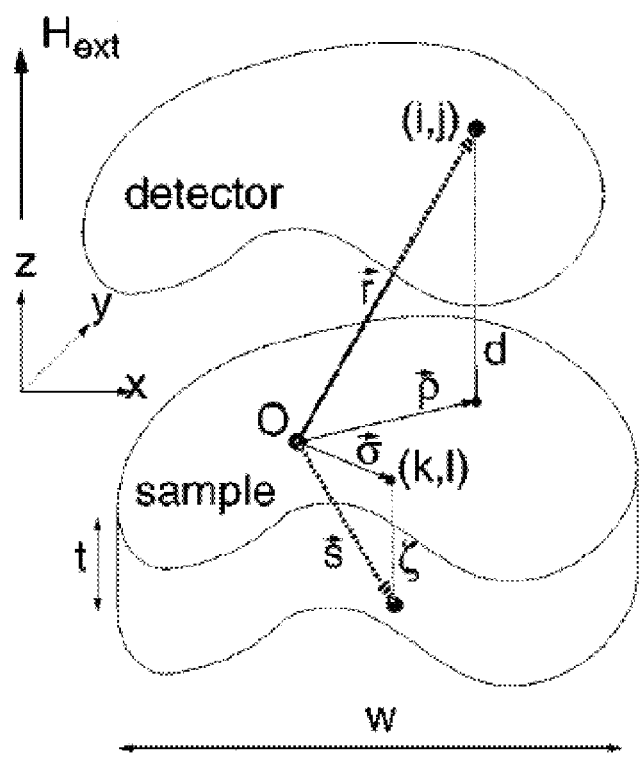
FIG. 11 is a schematic representation of a measurement layout of a detector plane and a position of a magneto-optical layer.

FIG. 11 is a schematic representation of a measurement layout of a detector plane and a position of a magneto-optical layer, in accordance with at least some embodiments described herein. In one example, the detector plane may be the plane in which the sample analyzer 208 resides and the magneto-optical layer is the magneto-optic film 212 of FIG. 2.

A point on the sample is located by co-ordinates (x,y), and due to currents flowing across the sample, a magnetic field distribution is generated across the sample. The magnetic field distribution across the sample is B(x,y), and a current distribution j(x,y) across the sample that produces the field distribution B(x,y) can be calculated. The sample can be divided into multiple portions (e.g., a smaller size of the portions results in higher resolution calculations), and in a center of each portion, an average B(x,y) is noted. Thus, the magnetic field distribution B(x,y) over the entire surface can be described by a matrix B, where each element of the matrix corresponds to a value of B(x,y) at a particular portion of the sample. Using the magneto-optical images, a local magnetic field distribution across the sample can be measured to determine the matrix B, and using a CCD to capture images, the images can be divided into portions, e.g., the CCD pixels. For example, in one embodiment, the image may comprise 512×512 pixels (e.g., small squares).

In one example, to extract a current pattern distribution from a given magnetic-field distribution, numerical deconvolution algorithms may be used. A magneto-optical (MO) image gives a distribution of a z-component of the magnetic field, and to determine the current pattern distribution, Biot-Savart's law can be inverted to convert the magnetic field distribution obtained from MO imaging into the current density distribution.

Using the schematic of the measurement geometry shown in FIG. 11, a flow of a current density $\vec{j}(\vec{s})$ through the sample induces a self-field $\vec{B}$ at any position $\vec{r}$ that can be expressed by the Biot-Savart law:

$$\vec{B}(\vec{r}) = \frac{1}{4\pi} \int_V \vec{j}(\vec{s}) \times \frac{\vec{r}-\vec{s}}{|\vec{r}-\vec{s}|^3} d^3s \qquad \text{Equation (1)}$$

The 2D-current pattern can be written in terms of the scalar field g as:

$$\vec{j}(\vec{s}) = \nabla_{\vec{s}} \times [g(\vec{s})\hat{z}] \qquad \text{Equation (2)}$$

Substituting Equation 2 in Equation 1 and using vector identities, the self-field of the sample can be expressed as:

$$\vec{B}(\vec{r}) = \frac{1}{4\pi} \int g(\vec{s}) \frac{3\hat{n}(\hat{z}\cdot\hat{n})-\hat{z}}{|\vec{r}-\vec{s}|^3} d^3s \qquad \text{Equation (3)}$$

where $$\hat{n} = \frac{(\vec{r} - \vec{s})}{|\vec{r} - \vec{s}|}.$$

Equation (3) illustrates that the self-field of a two dimensional current distribution $\vec{j}(\vec{s})$ can be decomposed into a spatial distribution of magnetic dipole moments of unit strength. Replacing $\vec{r}$ by $(\vec{\rho}, d)$ and s by $(\vec{\sigma}, \zeta)$ (as seen in FIG. 11), where d is the distance between the sample and detector and ζ is a depth of the sample as measured from the surface, Equation 3 can be rewritten as:

$$B_z(\vec{\rho}, d) = \frac{1}{4\pi} \int_s g(\vec{\sigma}) \int_0^t \frac{2(d+\zeta)^2 - |\vec{\rho} - \vec{\sigma}|^2}{[|\vec{\rho} - \vec{\sigma}|^2 + (d+\zeta)^2]^{5/2}} d\zeta d^2\sigma \quad \text{Equation (4)}$$

where the integral is over the sample surface S.

Within Equation (4), it is assumed that $g(\vec{\sigma}, \vec{\zeta}) = g(\vec{\sigma})$ (e.g., the current is uniform over the sample thickness). From the CCD, the Faraday rotated intensities are obtained as a 512×512 array of pixel values. As described above, this information can be converted into an array of magnetic field values $B_z(x,y)$. Writing the pixel values in the detector and sample as (i,j) and (x,y), respectively, the self-field detected at a distance d from the sample is given by:

$$B_z(i, j, d) = \frac{1}{4\pi} \sum_{k,l} g(k, l) \int_{k-1/2}^{k+1/2} \int_{l-1/2}^{l+1/2} \int_0^t \times \quad \text{Equation (5)}$$

$$\frac{2(d+\zeta)^2 - a^2(\xi - i)^2 - a^2(\eta - j)^2}{[(d+\zeta)^2 + a^2(\xi - i)^2 + a^2(\eta - j)^2]^{5/2}} d\zeta d\eta d\xi$$

with the pixel size along x and y in the detector being set equal to a, and replacing $d^2\sigma$ by $d\eta d\xi$. For a fixed a and d, the integral can be solved. Denoting the integral by M(i,j, k,l), Equation (5) can be expressed as:

$$B_z(i, j) = \frac{1}{4\pi} \sum_{k,l} M(i, j, k, l) g(k, l) \quad \text{Equation (6)}$$

which is a matrix equation of the form B=Mg. Thus, the magnetic field distribution matrix across the sample can be written as a product of two matrices. In examples described herein, systems and methods can be used to measure B, and M can be calculated. The matrix B=Mg can be inverted to determine g, which can be substituted into Equation (2) to determine the current density $\vec{j}(\vec{s})$, for example.

Thus, B=Mg, where M is a matrix that depends on a geometry of the sample and can be calculated as described above (e.g., shown as the integral of Equation (5)), and g is an unknown matrix to be determined after measuring B. The matrix M can be calculated, and then by matrix inversion of the equation B=Mg, the unknown matrix g is calculated. Once g is calculated, the value of g may be substituted into Equation (2) to determine a current density, for example.

Using example embodiments, a depth up to which magneto-optical imaging will reveal information depends on strength of the magnetic field generated by the currents flowing at a particular depth in the sample. Since the magnetic field sensitive element (e.g., the magneto-optic film) is located at a surface of the material being imaged, the magneto-optic film may be sensitive to fields generated by currents flowing up to a depth of about a few microns beneath the surface of the sample. For greater depth sensitivity, larger currents can be coupled through the sample so that larger currents are flowing at greater depths inside the sample. Magnetic fields present at the surface of the sample generated from currents flowing deep inside the surface of the sample should be within a sensitivity range of the magneto-optical film on the surface of the sample to enable magneto-optical imaging of the fields. For example, for about a few milliamps of current driven through the sample, a depth sensitivity may be about a few 10's of microns below the surface of the sample. For greater depth sensitivity, larger currents may give rise to a depth sensitivity of about a few 100 microns below the metal surface, for example.

In one embodiment, to perform depth sensitive imaging, imaging may begin with low DC current values to identify defects/damages occurring at a depth of within about a few tens of microns below the metal surface. The DC current can be gradually increased so that the sensitivity to image information at different depths can be gradually achieved. Using this example method may enable determining an approximate depth at which a damage in the metal is located.

In one embodiment, to identify a region with potential damage in a material, images from a potentially damaged area of the material can be compared to images from regions of undamaged areas. Making comparisons provides a verification of an amount of contrast and difference obtained in the magneto-optical images. This may help minimize errors in locating regions with damage in the material, for example. Prior to imaging any surface of a sample with magneto-optical imaging, the surface of the sample can be imaged with a polarization optical microscope, for example, for imperfections on the surface and also for crystalline defects (e.g., such as twin boundaries and dislocations) that could be misinterpreted in the MOI as damage or cracks.

As mentioned above, in various embodiments, the system may operate in one of two modes. In a first mode, or DC mode of operation, the system may directly image regions of material where weak structural damage has occurred (rather than indirectly infer a location). For example, the system may image a self magnetic field generated by a small DC electric current coupled through the material, as shown using the system in FIG. 2. In second mode of operation, or AC mode of operation, the system will function as an eddy current imager. The system may operate in each mode independently, or subsequently, so as to perform a DC imaging followed by an AC imaging for verification or vice versa.

Figure 12:
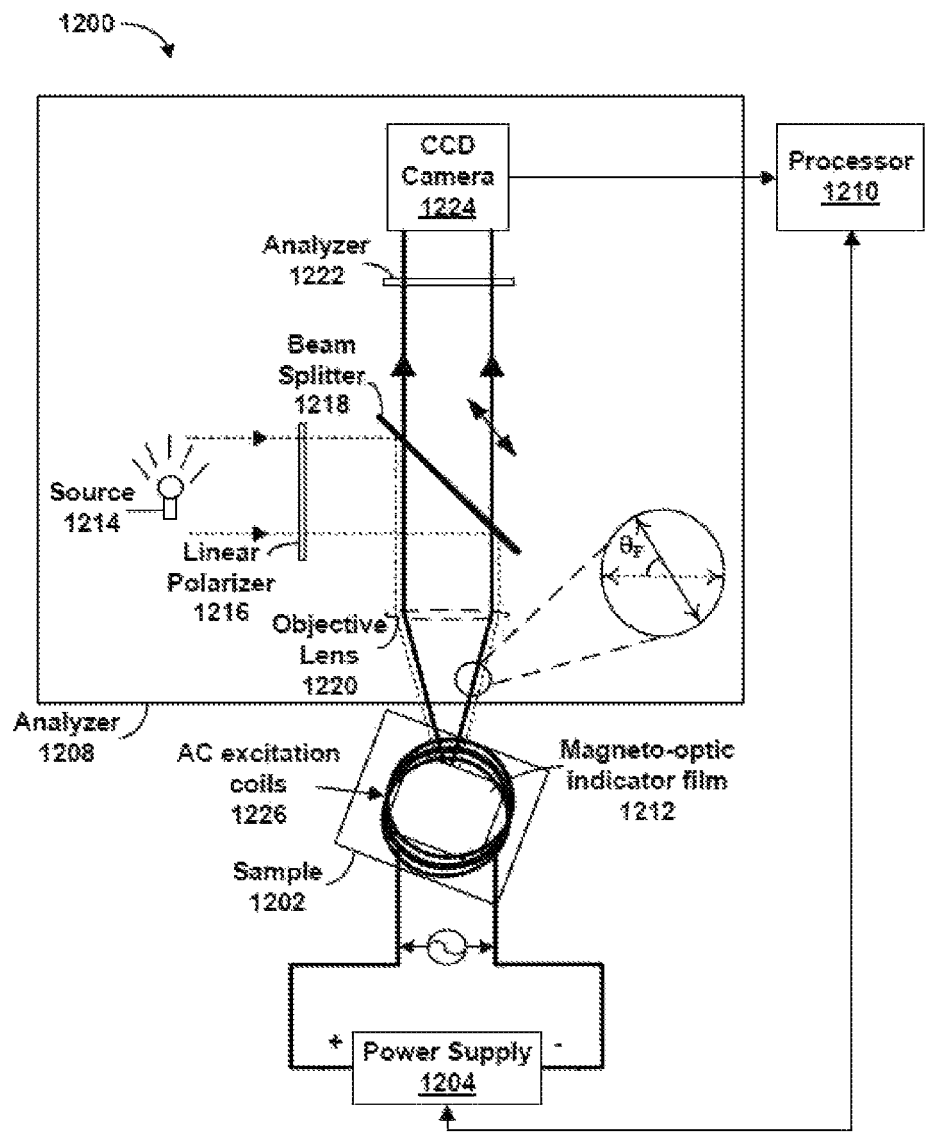
FIG. 12 is an example system that illustrates use of the system in an AC mode.

FIG. 12 is an example system 1200 that illustrates use of the system 1200 in an AC mode, arranged in accordance with at least some embodiments described herein. In some examples, system 1200 may include one or more functional or physical components such as a power supply 1204, a sample analyzer 1208, a processor 1210, a magneto-optic film 1212, a light source 1214, a linear polarizer 1216, a beam splitter 1218, an objective lens 1220, an analyzer 1222, an image capture device 1224, and AC excitation coils 1226. One or more of the described functions may be divided up into additional functional or physical components, or combined into fewer functional or physical components. In some further examples, additional functional and/or physical components may be added to the examples illustrated by FIG. 12. The system 1200 may be a portable, hand-held station, for example.

The system 1200 can be configured to image a magnetic field generated by eddy currents coupled through a sample 1202 using AC magnetic fields generated by the AC excitation coils 1226. The AC current can be provided by the power supply 1204 that is coupled to the AC excitation coils 1226 via electrical contacts (e.g., pins).

The sample analyzer 1208 is placed adjacent or substantially adjacent the sample 1202, and is coupled to the processor 1210. The sample analyzer 1208 can be configured to measure or detect characteristics of a magnetic field that is generated by the current coupled to/through the sample 1202. Example characteristics of the magnetic field that can be measured or detected by the sample analyzer 1208 include a presence of the magnetic field, a strength of the magnetic field, and changes in strength of the magnetic field.

The processor 1210 may receive outputs from the sample analyzer 1208, and may also be configured to control operation of the power supply 1204 and output an image indicating structural damage or defects in the surface of the sample 1202.

The magneto-optical film 1212 may be placed over the sample 1202 during measurements. The sample analyzer 1208 may include a window that is made out of the magneto-optical film 1212 which may be placed (or pressed) in contact with a surface of the sample 1202. Alternatively, the magneto-optical film 1212 may be separate from the sample analyzer 1208 and placed near or directly onto a surface of the sample 1202 to be analyzed.

The sample analyzer 1208 includes the light source 1214 (e.g., LED, light bulb, etc.). The light source 1214 can be configured to output light which passes through the linear polarizer 1216 and reflected by the beam splitter 1218 to reach the objective lens 1220. The objective lens 1220 focuses the light onto the magneto-optic film 1212, and may be a strain free objective lens, which helps to optically magnify a size of a portion of the sample 1202 that is being imaged and tested.

Light reflected by the magneto-optic film 1212 and pass back through the objective lens 1220 and through the beam splitter 1218 to the analyzer 1222. Light that passes through the analyzer 1222 is received at the image capture device 1224. The image capture device 1224 outputs to the processor 1210 for creating or generating the image.

The system 1200 may thus operate in a similar manner as the system 200, and similar components within each system may be the same or have similar functionality, for example, as described above.

The power source 1204 can be operated to provide an AC current to the AC excitation coils 1226. The AC excitation coils 1226 may be wound around the window that houses the magneto-optical film 1212, and eddy currents will be induced in the metallic surface using the AC excitation coils 1226. The AC excitation coils 1226 may be excited with either pulses of electric current or an AC electric current at a frequency level (e.g., in the range of few kHz) sent from the power source 1204. A time varying magnetic field generated from the AC excitation coils 1226 induces eddy currents in the metal surface below the AC excitation coils 1226.

Eddy currents generate magnetic fields that can be detected via the AC excitation coils 1226. Due to cracks or damages in the metallic surface, there will be discontinuities in the electrical conductivity of material in the sample 1202, which will interrupt a path of the eddy currents in the vicinity of the cracks. As a result, the self-magnetic field generated by the eddy currents around the vicinity of the cracks will be different compared to the self-magnetic field generated away from the vicinity of the cracks in the material. Due to the differences in the eddy current generated self-magnetic field distribution around the crack vicinity as compared to that away from the cracks, different contrasts in the magneto-optical images will be seen around the crack.

Results of the AC mode of operation may be dependent on geometry in which the eddy current is being induced, and thus, results may be difficult to interpret for complex geometry considerations. Interpretation of eddy current images may also be complex because the self-magnetic field generated due to the AC eddy currents depends on their paths, their shapes, and locations induced in the metal surface. In many instances, self-magnetic field images due to eddy currents may not necessarily imply regions with modified local electrical properties of the metal, and in some instances, such magnetic fields can also arise from complex eddy current paths present in the metal surface. Thus, information from the eddy current evaluation of a material with a complicated shape in the vicinity of a region with cracks can be complicated to interpret, and in some situations, may not provide accurate information or may not provide enough information alone to map regions with small changes in local electrical conductivity of the metal without having a physical damage.

In one embodiment, a system is described that is a combination of the system 200 in FIG. 2 and the system 1200 in FIG. 12, such that the system may operate in a DC or AC mode of operation. The AC mode of operation of the system 1200 may be useful in detecting regions of the metal surface that have actual physical damage, such as for example, hairline cracks on the surface or subsurface. The DC mode of operation may be more sensitive to mapping locations in which structural damage has just begun and physical properties of the metal in that region have begun to be slightly modified as compared to regions without any damage. Thus, a DC mode of operation may be used with the AC mode of operation. For example, the DC mode of operation may be performed before or after the AC mode of operation, and results from each can be used to verify locations of damage. In addition, the AC and DC mode of operation can be operated simultaneously, and provide enhanced sensitivity for imaging subsurface damages and cracks (e.g., cracks deeper inside the material) since an AC field may penetrate deeper into the material, for example.

In the DC mode of operation, a DC magnetic field distribution appears across a surface of the sample due to the distribution of a DC current flowing through the material. This magnetic field is imaged using MOI may have magnetic field distribution changes of the DC field around a damaged region as compared to the AC mode of operation, for example. Thus, the DC mode of operation may be utilized to provide imaging changes in paths of DC transport current distributed around flaws such that a unique and a high sensitivity instrument can detect and image locations of flaws in a material.

Thus, techniques (such as the AC mode of operation) can be used for mapping regions with actual physical damage such as cracks, and other techniques (such as the DC mode of operation) can be used to characterize and map regions with structural damage (e.g., not necessarily physical damage). Using DC and AC mode of operation simultaneously may also provide for sensitive depth sensitive imaging of damages and cracks, for example.

Embodiments disclosed herein may be utilized in a system that is portable, provides direct visualization of changes in a self magnetic field distribution around a region or location of damage in the material to lower or eliminate ambiguity in interpreting or finding the location of the defect, and enables application to complex geometrical shapes, for example.

Figure 13:
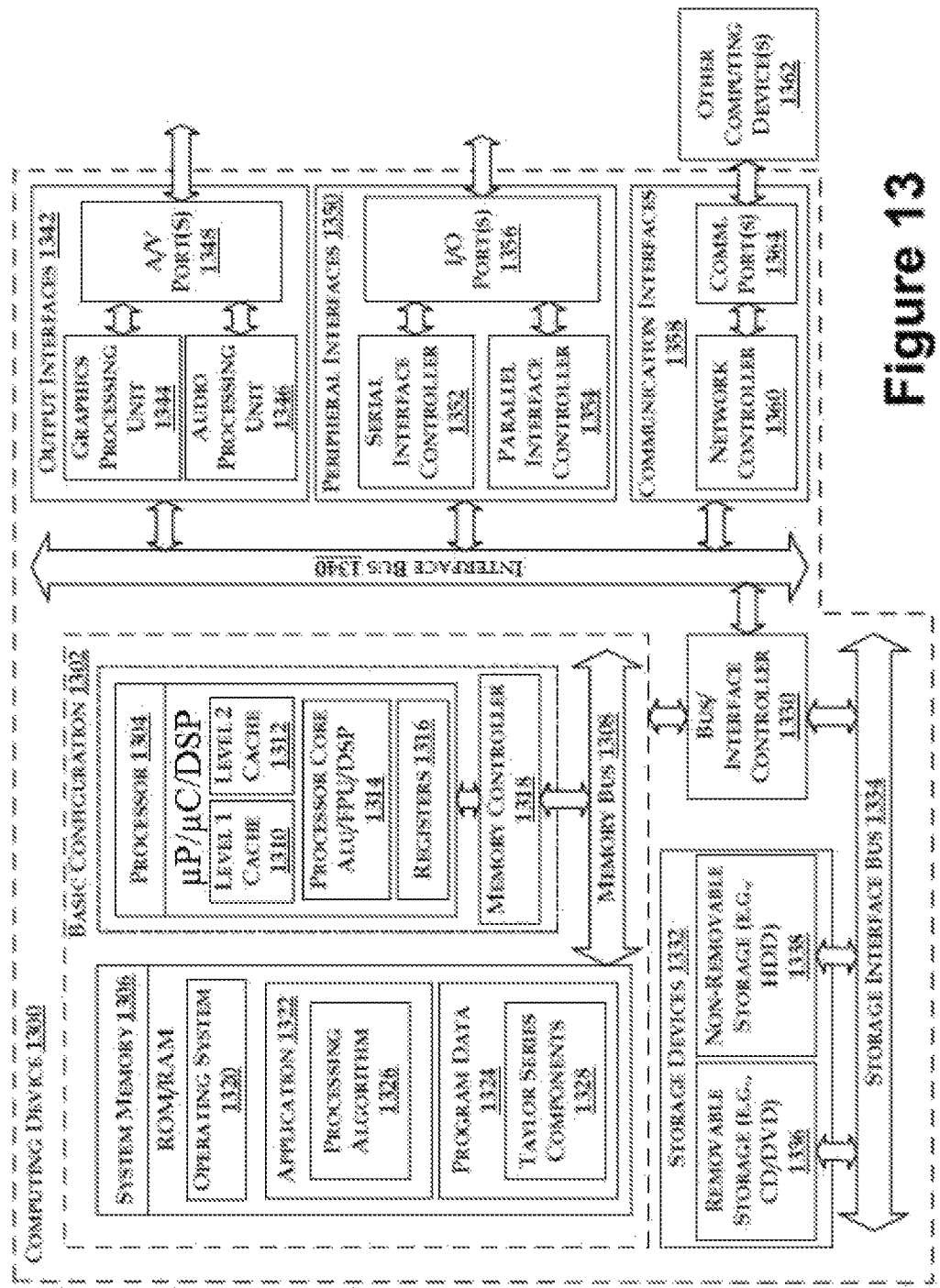
FIG. 13 is a block diagram illustrating an example computing device arranged for imaging characteristics of a sample, and/or identifying locations of defects or structural damage in a sample, all arranged in accordance with at least some embodiments described herein.

FIG. 13 is a block diagram illustrating an example computing device 1300 arranged for imaging characteristics of a sample, and/or identifying locations of defects or structural damage in a sample, in accordance with at least some embodiments described herein. In a very basic configuration 1302, computing device 1300 typically includes one or more processors 1304 and system memory 1306. A memory bus 1308 can be used for communicating between the processor 1304 and the system memory 1306.

Depending on the desired configuration, processor 1304 can be of any type including but not limited to a microprocessor (μP), a microcontroller (μC), a digital signal processor (DSP), or any combination thereof. Processor 1304 can include one or more levels of caching, such as a level one cache 1310 and a level two cache 1312, a processor core 1314, and registers 1316. The processor core 1314 can include an arithmetic logic unit (ALU), a floating point unit (FPU), a digital signal processing core (DSP Core), or any combination thereof. A memory controller 1318 can also be used with the processor 1304, or in some implementations, the memory controller 1318 can be an internal part of the processor 1304.

Depending on the desired configuration, the system memory 1306 can be of any type including but not limited to volatile memory (such as RAM), non-volatile memory (such as ROM, flash memory, etc.) or any combination thereof. System memory 1306 typically includes an operating system 1320, one or more applications 1322, and program data 1324. Application 1322 may include algorithms 1326 that may be arranged to perform any of the functions, procedures or methods described previously herein, depending on a configuration of the computing device 1300. Program Data 1324 may include values 1328 corresponding to images of characteristics of a sample, for example. In some example embodiments, application 1322 can be arranged to operate with program data 1324 on the operating system 1320, wherein the application and data may provide functionality as described previously herein. This described basic configuration is illustrated in FIG. 13 by those components within dashed line 1302.

Computing device 1300 can have additional features or functionality, and additional interfaces to facilitate communications between the basic configuration 1302 and any required devices and interfaces. For example, a bus/interface controller 1330 can be used to facilitate communications between the basic configuration 1302 and one or more data storage devices 1332 via a storage interface bus 1334. The data storage devices 1332 can be removable storage devices 1336, non-removable storage devices 1338, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media can include volatile and nonvolatile, removable and non-removable media implemented in any method or technology for storage of information, such as computer readable instructions, data structures, program modules, or other data.

System memory 1306, removable storage 1336 and non-removable storage 1338 are all examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 1300. Any such computer storage media can be part of device 1300.

Computing device 1300 can also include an interface bus 1340 for facilitating communication from various interface devices (e.g., output interfaces, peripheral interfaces, and communication interfaces) to the basic configuration 1302 via the bus/interface controller 1330. Example output interfaces 1342 include a graphics processing unit 1344 and an audio processing unit 1346, which can be configured to communicate to various external devices such as a display or speakers via one or more A/V ports 1348. Example peripheral interfaces 1350 include a serial interface controller 1352 or a parallel interface controller 1354, which can be configured to communicate with external devices such as input devices (e.g., keyboard, mouse, pen, voice input device, touch input device, etc.) or other peripheral devices (e.g., printer, scanner, etc.) via one or more I/O ports 1356. An example communication interface 1358 includes a network controller 1360, which can be arranged to facilitate communications with one or more other computing devices 1362 over a network communication via one or more communication ports 1364. The communication connection is one example of a communication media. Communication media may typically be embodied by computer readable instructions, data structures, program modules, or other data in a modulated data signal, and includes any information delivery media. A "modulated data signal" can be a signal that has one or more of its characteristics set or changed in such a manner as to encode information in the signal. By way of example, and not limitation, communication media can include wired media such as a wired network or direct-wired connection, and wireless media such as acoustic, radio frequency (RF), infrared (IR) and other wireless media. In some examples, the term computer readable media as used herein can include storage media, communication media, or both.

Computing device 1300, and/or portions of computing device, can be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 1300 can also be implemented as a personal computer including both laptop computer and non-laptop computer configurations. Images of data captured can be transmitted over the internet to multiple users existing at remote locations from the sample or the damage evaluation site, for example.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general, such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth."

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of identifying characteristics of a sample, the method comprising:
coupling a current that includes a first direct current component and a second direct current component to the sample such that a magnetic field is generated across a surface of the sample;
providing a linearly polarized source light to a magneto-optic film that is positioned substantially adjacent to the surface of the sample, wherein at least a portion of the linearly polarized source light is reflected by the magneto-optic film as reflected light, and wherein the reflected light includes:
first reflected light with a first plane of polarization rotated from a linearly polarized source light's plane of polarization, and
second reflected light with a second plane of polarization rotated from the linearly polarized source light's plane of polarization;
using magneto-optical imaging of at least a portion of the first reflected light and a portion of the second reflected light:
capturing a first set of images of the sample when the first direct current component flows through the sample in a first direction; and
capturing a second set of images of the sample when the second direct current component flows through the sample in a second direction, wherein the second direction is opposite to the first direction;
summing the first set of images to form a first image output;
summing the second set of images to form a second image output;

determining a differential image as a difference between the first image output and the second image output; and identifying the characteristics of the sample based on the first reflected light and the second reflected light.

2. The method of claim 1, further comprising:
capturing a distribution of Faraday rotation intensities with the magneto-optical imaging, where the magnetic field creates the distribution of Faraday rotation intensities at different locations of the sample.

3. The method of claim 1, wherein the second plane of polarization of the second reflected light is rotated by an amount proportional to a magnitude of the magnetic field present at a location of the sample where the linearly polarized source light is reflected by the magneto-optic film.

4. The method of claim 1, wherein the second plane of polarization of the second reflected light is rotated to an extent determined by the magnetic field generated across the surface of the sample.

5. The method as in claim 1, further comprising identifying a damage associated with a region of the sample by evaluating variations in bright and dark contrasts in each of the first set of images and the second set of images to identify changes in a current flow path around the region of the sample associated with the damage.

6. The method of claim 1, wherein the current comprises a direct current between 1 mA and 100 mA.

7. The method of claim 1, wherein the current further includes an alternating current (AC) component.

8. The method of claim 7, wherein coupling the current further comprises coupling the AC component and the first direct current component through the sample in the first direction.

9. The method of claim 7, wherein coupling the current to the sample further comprises
coupling the AC component and the second direct current component through the sample in the second direction.

10. The method of claim 7, wherein coupling the current to the sample further comprises inducing eddy currents in the sample to generate the magnetic field across the sample based on the AC component, and wherein a distribution of the magnetic field across the sample varies due to the characteristics of the sample; and
the method further comprises detecting the magnetic field generated by the eddy currents with excitation coils coupled to the magneto-optic film.

11. A method of identifying characteristics of a sample, the method comprising:
providing a linearly polarized source light to a magneto-optic film, wherein the magneto-optic film is arranged substantially adjacent to a surface of the sample, wherein the magneto-optic film is effective to reflect at least a portion of the linearly polarized source light;
coupling a first current through the sample in a first direction to generate a first magnetic field across the surface of the sample, wherein characteristics of the first magnetic field vary due to the first current and the characteristics of the sample;
capturing a first set of images of the sample using magneto-optical imaging of at least a portion of first reflected light reflected from the linearly polarized source light incident on the magneto-optic film based on the first magnetic field, wherein the first reflected light includes second reflected light and third reflected light, the second reflected light with a first plane of polarization rotated from a linearly polarized source light's plane of polarization, the third reflected light with a second plane of polarization rotated from the linearly polarized source light's plane of polarization, the first plane of polarization and the second plane of polarization are rotated with respect to the linearly polarized source light in presence of the first magnetic field at a first location of the sample where the linearly polarized source light is reflected by the magneto-optic film;
summing the first set of images to form a first image output;
coupling a second current through the sample in a second direction to generate a second magnetic field across the surface of the sample, wherein characteristics of the second magnetic field vary due to the second current and the characteristics of the sample;
capturing a second set of images of the sample using magneto-optical imaging of at least a portion of fourth reflected light reflected from the linearly polarized source light incident on the magneto-optic film based on the second magnetic field, wherein the fourth reflected light includes fifth reflected light and sixth reflected light, the fifth reflected light with a third plane of polarization rotated from the linearly polarized source light's plane of polarization, the sixth reflected light with a fourth plane of polarization rotated from the linearly polarized source light's plane of polarization, the third plane of polarization and the fourth plane of polarization are rotated with respect to the linearly polarized source light in presence of the second magnetic field at a second location of the sample where the linearly polarized source light is reflected by the magneto-optic film, and wherein the second magnetic field is generated based on the characteristics of the sample and the second current;
summing the second set of images to form a second image output; and
determining a differential image as a difference between the first image output and the second image output.

12. The method of claim 11, wherein the first location is substantially the same as the second location.

13. The method of claim 11, wherein one or more of the first current and/or the second current correspond to a direct current (DC).

14. A system effective to identify characteristics of a sample, the system comprising:
a power supply configured to couple a current that includes a first direct current component and a second direct current component to the sample to generate a magnetic field across a surface of the sample;
a magneto-optic film arranged substantially adjacent to the surface of the sample;
a sample analyzer configured to provide a linearly polarized source light to the magneto-optic film, wherein at least a portion of the linearly polarized light is reflected by the magneto-optic film as reflected light, and wherein the reflected light includes:
first reflected light with a first plane of polarization rotated from a linearly polarized source light's plane of polarization, and
second reflected light with a second plane of polarization rotated from the linearly polarized source light's plane of polarization, wherein the sample analyzer comprises a camera configured to:
capture a first set of images of the sample when the first direct current component flows through the sample in a first direction, using magneto-optical imaging of the first reflected light and the second reflected light, and capture a second set of images of the sample when the second direct current component flows through the sample in a second direction, using the magneto-optical imaging of the first reflected light and the second reflected light, wherein the second direction is opposite to the first direction; and a processor configured to:
sum the first set of images to form a first image output,
sum the second set of images to form a second image output,
determine a differential image as a difference between the first image output and the second image output, and
identify the characteristics of the sample based on the first reflected light and the second reflected light.

15. The system of claim 14, wherein the processor is further configured to generate a spatial map of distribution of the magnetic field generated from the current to enable identification of locations with structural damage in the sample.

16. The system of claim 14, wherein the sample analyzer further comprises a beam splitter configured to:
receive the linearly polarized source light, and
direct the linearly polarized source light to the magneto-optic film.

17. The system of claim 14, wherein the sample analyzer further comprises an objective lens configured to:
receive the linearly polarized source light, and
direct the linearly polarized source light to the magneto-optic film.

18. The system of claim 14, wherein the sample analyzer further comprises an analyzer that has a plane of polarization substantially perpendicular in orientation to the linearly polarized source light's plane of polarization, wherein the analyzer is configured to:
receive the first reflected light and the second reflected light, and
transmit the first reflected light and the second reflected light to the camera.

19. The system of claim 14, wherein the magneto-optic film is a Bismuth doped yttrium-iron-garnet single crystal film (Bi:YIG), and wherein the magneto-optic film includes a layer of Bi-doped yttrium iron garnet film, a gallium-gadolinium-garnet (GGG) substrate layer, and a mirror layer.

20. The system of claim 14, wherein the magneto-optic film includes materials that are adapted to produce Faraday rotations of the linearly polarized source light in presence of magnetic fields such that the magneto-optic film is effective to rotate the linearly polarized source light's plane of polarization by an amount proportional to a magnitude of the magnetic field present at a location of the sample where the linearly polarized source light is reflected by the magneto-optic film.

21. The system of claim 14, wherein the current further includes an alternating current (AC) component.

22. The system of claim 21,
wherein the power supply is further configured such that the current coupled to the sample induces eddy currents in the sample to generate the magnetic field across the sample, and
wherein the system further comprises excitation coils coupled to the magneto-optic film and configured to detect the magnetic field generated by the eddy currents.

* * * * *

UNITED STATES PATENT AND TRADEMARK OFFICE
CERTIFICATE OF CORRECTION

PATENT NO. : 9,778,202 B2  
APPLICATION NO. : 13/878944  
DATED : October 3, 2017  
INVENTOR(S) : Banerjee et al.

Page 1 of 1

It is certified that error appears in the above-identified patent and that said Letters Patent is hereby corrected as shown below:

In Column 5, Line 64, delete "min" and insert -- nm --, therefor.

In Column 7, Line 46, delete "aluminum" and insert -- aluminium --, therefor.

Signed and Sealed this  
Twenty-second Day of May, 2018

Andrei Iancu  
*Director of the United States Patent and Trademark Office*